United States Patent
Parkinson et al.

(10) Patent No.: US 6,697,668 B2
(45) Date of Patent: Feb. 24, 2004

(54) OCULAR IONTOPHORETIC DEVICE AND METHOD FOR USING THE SAME

(75) Inventors: Thomas M. Parkinson, White Salmon, WA (US); Malgorzata Szlek, Salt Lake City, UT (US); Lindsay B. Lloyd, Salt Lake City, UT (US)

(73) Assignee: Iomed, Inc., Salt Lake City, UT (US)

( * ) Notice: Subject to any disclaimer, the term of this patent is extended or adjusted under 35 U.S.C. 154(b) by 0 days.

(21) Appl. No.: 09/769,658

(22) Filed: Jan. 25, 2001

(65) Prior Publication Data

US 2002/0099357 A1 Jul. 25, 2002

(51) Int. Cl.$^7$ ............................... A61N 5/00
(52) U.S. Cl. .................. 604/20; 128/770; 606/3; 606/9; 606/10; 607/88
(58) Field of Search .............. 604/20, 21; 128/770; 606/2–17; 607/88–89

(56) References Cited

U.S. PATENT DOCUMENTS

| | | | |
|---|---|---|---|
| 4,564,016 A | | 1/1986 | Maurice et al. |
| 5,476,511 A | * | 12/1995 | Gwon et al. ............... 356/317 |
| 5,904,144 A | * | 5/1999 | Hammang et al. .......... 128/898 |
| 6,315,772 B1 | * | 11/2001 | Marchitto et al. ............ 604/21 |

FOREIGN PATENT DOCUMENTS

| | | |
|---|---|---|
| FR | 98-00009 | 1/1998 |
| RU | 995783 | 2/1983 |

OTHER PUBLICATIONS

Sarraf, et al, *The Role of Iontophresis in Ocular Drug Delivery*, J. Ocular Pharmacol, vol. 10, p. 69–81 (1994).
Kiselev, et al, *Procedure for the Administration of Drugs in Gels to Ocular Tissues Through the Use of Electrophoresis*, Procedural Recommendation OMCK (1984).
F. Behar–Cohen, *Iontophoresis of Dexamethasone in the Treatment of Endotoxin–Induced–Uveitis in Rats*, Exp. Eye Res., vol. 65, p. 533–545 (1997).
Lebedev, *Electrophoretic Trials in the Early Diagnosis of Primary Glaucoma*, Dissertation OMSK (1983).

* cited by examiner

Primary Examiner—Steven O. Douglas
(74) Attorney, Agent, or Firm—Factor & Partners

(57) ABSTRACT

An ocular iontophoretic device for delivering an interferon to an affected area of a living being's eye comprising an active electrode assembly associated with a matrix, wherein the matrix includes an interferon capable of treating viral, immunoregulatory, and/or neovascularization conditions.

A method for treating an affected area of a living being's eye comprising the steps of: associating an interferon with an ocular iontophoretic device; positioning at least a portion of the ocular iontophoretic device on the eye of a living being; and iontophoretically delivering the interferon to an affected area of the living being's eye.

36 Claims, 1 Drawing Sheet

OCULAR IONTOPHORETIC DEVICE AND METHOD FOR USING THE SAME

BACKGROUND OF THE INVENTION

1. Field of the Invention

The present invention relates in general to an ocular iontophoretic device, and more particularly, to an ocular iontophoretic device which, upon association with the eye of a living being, and application of an electrical potential difference, iontophoretically delivers an interferon into the living being's eye, thereby treating viral, immunoregulatory, and/or neovascularization conditions.

2. Background Art

Interferons have been known in the art for years, and have been shown to possess antiviral as well as immunoregulatory activities. More recently, research has been initiated relative to treating numerous conditions characterized by or arising from neovascularization in the tissues and structures of the eye, including Age-Related Macular Degeneration (AMD). While administering an interferon has been identified as a promising mechanism to remedy the above-identified conditions, delivering an interferon to an affected area of a living being's eye remains problematic. Indeed, known prior art devices and associated methods of administering an interferon, identified hereinbelow, are replete with drawbacks and disadvantages.

For example, delivering an interferon to an affected, local area of a living being's eye using a systemic delivery method is problematic because of the many conventional side effects associated with systemic delivery, including depression, headache, arthritis-like joint pain, flu-like symptoms, unnecessary medicament exposure to unaffected areas, toxicity buildup, and concentration control.

Local delivery of an interferon via interocular injection is problematic because of the opportunity for, among other things, retinal detachment, bleeding into the interior of the eye, increased interocular pressure, and increased risk of secondary infection. Although perhaps justifiable for occasional acute conditions, these risk factors render interocular injection undesirable as a delivery mode for chronic administration. Furthermore, interocular injections can be scary, unpleasant, and painful for the patient.

In addition to the above-identified problems associated with interocular injection, peribular or subconjuctival injection of an interferon is problematic, because such injections may not deliver sufficient quantities to the interior of the eye. Moreover, peribular or subconjuctival injections are demanding of the physician inasmuch as placement of the needle requires an extremely high level of precision.

Topical administration of an interferon to an affected, local area of a living being's eye is problematic due to its ineffectiveness for many applications, including affected areas in the back of the eye.

SUMMARY OF THE INVENTION

The present invention is directed to an ocular iontophoretic device for delivering an interferon to an affected area of a living being's eye comprising an active electrode assembly associated with a matrix, wherein the matrix includes an interferon capable of treating viral, immunoregulatory, and/or neovascularization conditions.

In a preferred embodiment of the present invention, the matrix includes an interferon selected from the group consisting of an alpha-interferon, a beta-interferon, a gamma-interferon, and mixtures thereof. In this embodiment the interferon may include a single type of beta-interferon, such as beta-1b interferon.

In another preferred embodiment of the present invention, the interferon comprises one or more natural or synthetic proteins having a molecular weight ranging from approximately 15,000 to approximately 25,000 daltons.

In yet another preferred embodiment of the present invention, the interferon is formulated in an approximately 20 mM sodium acetate and approximately 208 mM arginine hydrochloride buffer. In this embodiment the buffer may range in pH from approximately 4.0 to approximately 6.0, and more preferably from approximately 4.5 to approximately 5.0.

Preferably, the affected area of the eye is selected from at least one of the group consisting of the vitreous humor, retina, choroid, circulation of the retina, circulation of the choroid, and sclera.

In accordance with the present invention, the ocular iontophoretic device further comprises a counter electrode assembly, wherein the counter electrode assembly is configured for completing an electrical circuit between the active electrode assembly and an energy source, and an energy source for generating an electrical potential difference.

The present invention is also directed to an ocular iontophoretic device for delivering an interferon to an affected area of a living being's eye, comprising: (a) a matrix, wherein the matrix is capable of temporarily retaining a solution having an interferon; (b) an active electrode assembly associated with the matrix, wherein the active electrode assembly is configured for iontophoretically delivering the interferon to the affected area of the living being's eye; (c) a counter electrode assembly, wherein the counter electrode assembly is configured for completing an electrical circuit between the active electrode assembly and an energy source; and (d) an energy source for generating an electrical potential difference. It is also contemplated that the ocular iontophoretic device comprise a reservoir, wherein the reservoir includes an interferon capable of treating viral, immunoregulatory, and/or neovascularization conditions.

The present invention is further directed to a method for treating an affected area of a living being's eye comprising the steps of: (a) associating an interferon with an ocular iontophoretic device; (b) positioning at least a portion of the ocular iontophoretic device on the eye of a living being; and (c) and iontophoretically delivering the interferon to an affected area of the living being's eye.

In a preferred embodiment of the present invention, the step of associating the interferon includes the step of associating an interferon capable of treating viral, immunoregulatory, and/or neovascularization conditions.

In another preferred embodiment of the present invention, the step of iontophoretically delivering the interferon includes the step of iontophoretically delivering the interferon to at least one of the group consisting of the vitreous humor, retina, choroid, circulation of the retina, circulation of the choroid, and sclera.

In yet another preferred embodiment of the present invention, the step of iontophoretically delivering the interferon includes the step of iontophoretically loading a sclera of the living being's eye with the interferon for prolonged delivery into back regions of the living being's eye.

Preferably, the step of iontophoretically delivering the interferon, includes the step of iontophoretically delivering the interferon at a current between approximately 0.5 mA and approximately 4 mA for a period of between approximately 5 and approximately 20 minutes.

In accordance with the present invention, the step of iontophoretically delivering the interferon includes the step of delivering the interferon using positive polarity electrical current.

In a preferred embodiment of the present invention, the step of positioning at least a portion of the ocular iontophoretic device on the eye of a living being includes the step of applying at least a portion of the ocular iontophoretic device to a conjunctival surface in a region of a pars planum and insertions of an anterior cilliary artery.

The present invention is further directed to a method for treating a viral, immunoregulatory, and/or neovascularization condition within an affected area of a living being's eye comprising the steps of: (a) associating an interferon with a matrix of an ocular iontophoretic device; (b) associating the ocular iontophoretic device having an active electrode assembly with the eye of the living being; (c) iontophoretically delivering an effective amount of the interferon to an affected area of the living being's eye having a viral, immunoregulatory, and/or neovascularization condition; and (d) treating the affected area of the living being's eye, and, in turn, reducing or eliminating effects of a viral, immunoregulatory, and/or condition.

BRIEF DESCRIPTION OF THE DRAWINGS

The invention will now be described with reference to the drawings wherein.

DETAILED DESCRIPTION OF THE INVENTION

Figure 1:
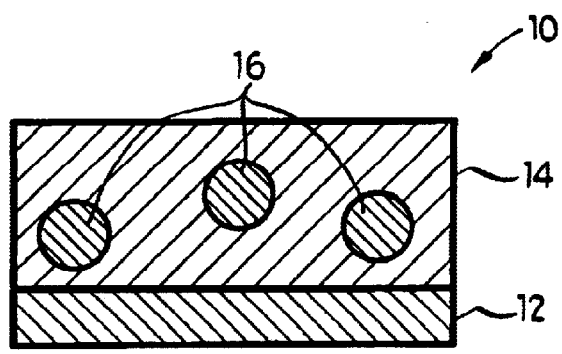
FIG. 1 of the drawings is a cross-sectional schematic representation of a first embodiment of an ocular iontophoretic device fabricated in accordance with the present invention.

While this invention is susceptible of embodiment in many different forms, there is shown in the drawings and will herein be described in detail several specific embodiments with the understanding that the present disclosure is to be considered as an exemplification of the principles of the invention and is not intended to limit the invention to the embodiments illustrated.

Referring now to the drawings and to FIG. 1 in particular, a first embodiment of an ocular iontophoretic device 10 is shown, which generally comprises active electrode assembly 12 and matrix 14. It will be understood that FIG. 1 is merely a cross-sectional schematic representation of ocular iontophoretic device 10. As such, some of the components have been distorted from their actual scale for pictorial clarity. As will be discussed in greater detail below, ocular iontophoretic device 10 is configured for delivering an interferon to an affected area of a living being's eye, thereby treating viral, immunoregulatory, and/or neovascularization conditions. By iontophoretically administering an interferon to the affected area of the eye, diseases associated with, among other things, viral, immunoregulatory, and/or neovascularization conditions can be efficiently remedied— especially including diseases of the eye wherein the affected area is toward the back of the eye, or generally proximate the optic nerve. Ocular iontophoretic device 10 offers many advantages over the previously discussed prior art devices and associated methods, including, but not limited to, simultaneous enablement of non-invasive and deep interferon delivery, non-invasive local delivery of an effective, therapeutic level of interferon while minimizing systemic concentrations, and enablement of sclera loading for prolonged delivery into regions in the back of the eye.

Active electrode assembly 12 generally comprises a conductive material, which upon application of an electrical potential difference thereto, drives an ionic interferon (i.e. an ionic medicament), received from matrix 14 and delivers the interferon into predetermined tissues and surrounding structures of a living being. It will be understood that active electrode assembly 12 may comprise an anode or a cathode depending upon whether the medicament is cationic or anionic in form. It will be further understood that active electrode assembly may include an open-faced or high current density electrode. As would be readily understood to those having ordinary skill in the art, any one of a number of conventional active electrode assemblies are contemplated for use in accordance with the present invention. The only contemplated limitation relative to active electrode assembly 12 is that it must be geometrically and compositionally compatible for ocular applications of living beings, most relevantly, humans.

Matrix 14 extends contiguously from active electrode 12, and is preferably fabricated from a material capable of temporarily retaining ionic interferon 16 in solution. The solution may also contain supplemental agents, such as electrolytes, stability additives, medicament preserving additives, pH regulating buffers, etc. Matrix 14 may comprise, for example, a natural or synthetic amorphous member, a natural or synthetic sponge pad, a natural or synthetic lint free pad, a natural or synthetic low particulate member—just to name a few. Indeed, numerous other materials that would be known to those having ordinary skill in the art having the present disclosure before them are likewise contemplated for use. As with active electrode assembly 12, the only contemplated limitation relative to matrix 14 is that it must be geometrically and compositionally compatible for ocular applications of living beings, most relevantly, humans.

Interferon 16 is retained within matrix 14. In accordance with the present invention, ionic medicament 16 comprises an interferon which is capable of treating viral, immunoregulatory, and/or neovascularization conditions. Such an interferon consists of one or more proteins, having a molecular weight ranging from approximately 15,000 to approximately 25,000 daltons. Preferred interferons include alpha, beta, and gamma interferons. Examples of suitable interferons for use in accordance with the present invention include: interferon alfa-2A available from Roche Pharmaceuticals of Nutley, N.J.; interferon alfa-2B available from Schering Corporation of Kenilworth, N.J.; interferon alfacon-1 available from Amgen Inc., of Thousand Oaks, Calif.; interferon alfa-N3 available from Interferon Sciences, Inc., of New Brunswick, N.J.; interferon beta-1A available from Biogen, Inc., of Cambridge, Mass.; interferon beta-1B available from Berlex Laboratories of Richmond, Calif.; and interferon gamma-1B available from InterMune Pharmaceuticals, Inc., of Palo Alto, Calif. Other interferons that would be known to those having ordinary skill in the art having the present disclosure before them are likewise contemplated for use.

Figure 2:
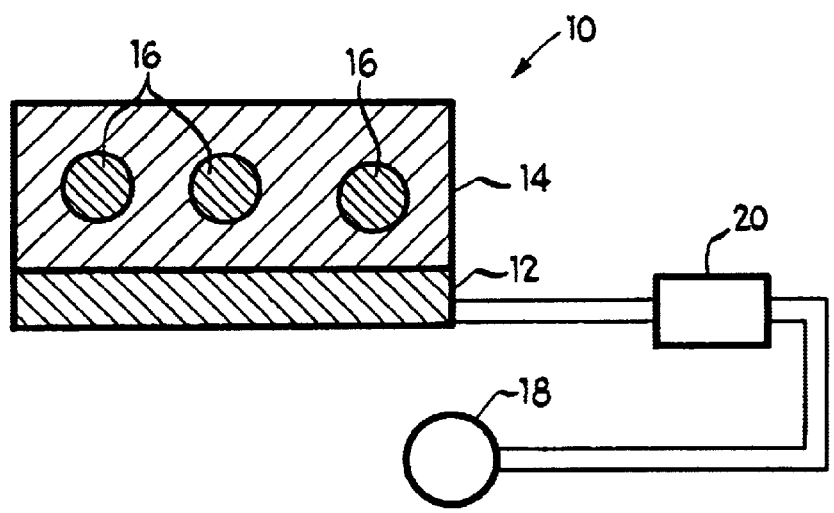
FIG. 2 of the drawings is a cross-sectional schematic representation of a first embodiment of an ocular iontophoretic device fabricated in accordance with the present invention showing the association of a counter electrode assembly and an energy source.

As is shown in FIG. 2, ocular iontophoretic device 10 may also include counter electrode assembly 18 and energy source 20. Counter electrode assembly 18 may be housed within ocular iontophoretic device 10, or alternatively, may be remotely associated with ocular iontophoretic device 10 via conventional electrical conduit. Counter electrode assembly 18 is configured for completing an electrical circuit between active electrode assembly 12 and an energy source 20. As with active electrode 12, counter electrode 18 may comprise an anode or a cathode depending upon whether the medicament is cationic or anionic in form. As would be readily understood to those having ordinary skill in the art, any one of a number of counter electrodes are contemplated for use in accordance with the present invention.

Similarly to counter electrode assembly 18, energy source 20 may be housed within ocular iontophoretic device 10, or alternatively, may be remotely associated with ocular iontophoretic device 10 via conventional electrical conduit. Energy source 20 preferably supplies low voltage constant direct current between approximately 0.5 milliamps (mA) and approximately 4 mA for generating an electrical potential difference. The energy source may also provide for an initial higher voltage during current ramp-up to break down higher initial tissue resistance as in commercial power supply units used for transdermal iontophoresis. For purposes of the present disclosure, energy source 20 may include one or more primary or secondary electrochemical cells. While specific examples of energy source 20 have been disclosed, for illustrative purposes only, it will be understood that other energy sources known to those having ordinary skill in the art having the present disclosure before them are likewise contemplated for use.

Figure 3:
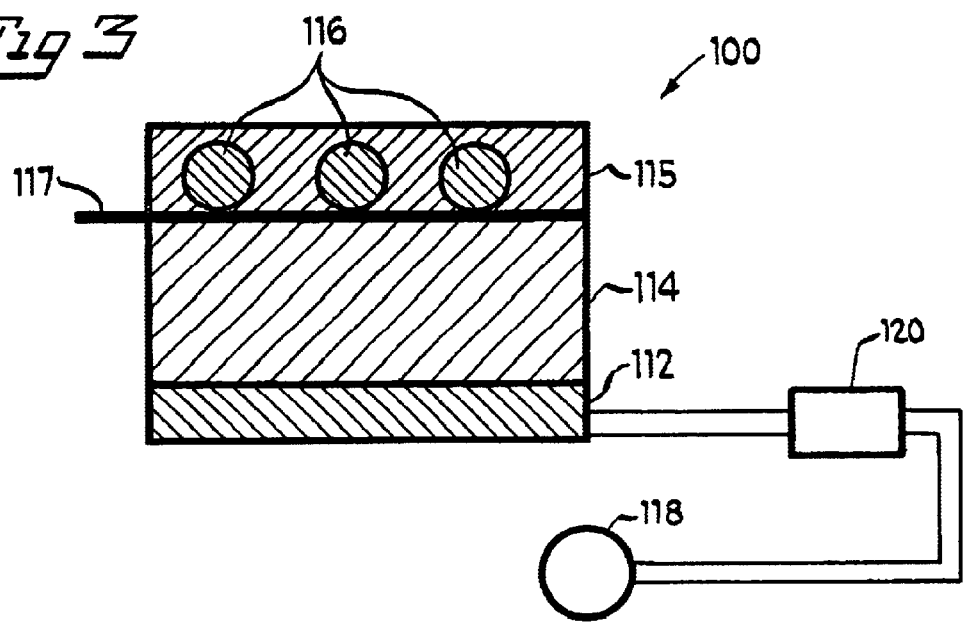
FIG. 3 of the drawings is a cross-sectional schematic representation of a second embodiment of an ocular iontophoretic device fabricated in accordance with the present invention.

Referring now to the drawings and to FIG. 3 in particular, a second embodiment of an ocular iontophoretic device 100 is shown, which generally comprises active electrode assembly 112, matrix 114, reservoir 115, counter electrode assembly 118, and energy source 120. It will be understood that active electrode assembly 112, matrix 114, counter electrode assembly 118, and energy source 120, are configured analogously to previously discussed active electrode assembly 12, matrix 14, counter electrode assembly 18, and energy source 20, respectively. Ocular iontophoretic device 100 is configured for delivering an interferon to an affected area of a living being's eye for treating viral, immunoregulatory, and/or neovascularization conditions therein.

Reservoir 115 includes an interferon 116, in solution, which is capable of treating viral, immunoregulatory, and/or neovascularization conditions. Reservoir 115 may include a releasable cover member 117 which, upon articulation, releases interferon 116 into matrix 114. Such a release cover enables prompt delivery of the interferon with very little device preparation.

The present invention is also directed to a method for treating an affected area of a living being's eye comprising the following steps. First, an interferon is associated with an ocular iontophoretic device. Preferably the interferon is metered from a syringe or single unit dose. Second, at least a portion of the ocular iontophoretic device is positioned on the eye of a living being. Finally, the interferon is iontophoretically delivered to an affected area of the living being's eye. Preferably, the delivery lasts for between approximately 5 and approximately 20 minutes. Compared to prior art administration or delivery methods, the present invention enables a generally painless, non-invasive and deep delivery of the interferon. Moreover, the interferon is locally delivered to an affected area of a living being's eye at an effective, therapeutic level. Preferred ocular delivery regions include the vitreous humor, retina, choroid, circulation of the retina, circulation of the choroid, and sclera. It is likewise contemplated that delivery to front regions of the eye may be administered.

The present invention is also directed to a method for treating viral, immunoregulatory, and neovascular conditions within an affected area of a living being's eye comprising the following steps. First, an interferon is associated with the matrix of the ocular iontophoretic device. Second, an effective amount of the interferon is iontophoretically delivered to an affected area of the living being's eye. Third, the affected area is treated, thereby reducing or eliminating the effects of a viral, immunoregulatory, and/or condition within an affected area of a living being's eye.

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. An active electrode assembly for use in an ocular iontophoretic device, comprising:
   an active electrode in electrical communication with a matrix, wherein the matrix is capable of temporarily retaining an interferon therein; and
   an interferon capable of treating viral, immunoregulatory, and/or neovascularization conditions retained within the matrix.

2. The active electrode assembly according to claim 1, wherein the matrix includes an interferon selected from the group consisting of an alpha-interferon, a beta-interferon, a gamma-interferon, and mixtures thereof.

3. The active electrode assembly according to claim 1, wherein the matrix includes a beta-interferon.

4. The active electrode assembly according to claim 1, wherein the matrix includes a beta-1b interferon.

5. The active electrode assembly according to claim 1, wherein the interferon comprises one or more natural or synthetic proteins having a molecular weight ranging from between approximately 15,000 to approximately 25,000 daltons.

6. The active electrode assembly according to claim 1, wherein the interferon is formulated in an approximately 20 mM sodium acetate and approximately 208 mM arginine hydrochloride buffer.

7. The active electrode assembly according to claim 6, wherein the buffer ranges in pH from approximately 4.0 to approximately 6.0.

8. The active electrode assembly according to claim 7, wherein the buffer ranges in pH from approximately 4.5 to approximately 5.0.

9. The active electrode assembly according to claim 1, wherein the affected area of the eye is selected from at least one of the group consisting of the vitreous humor, retina, choroid, circulation of the retina, circulation of the choroid, and sclera.

10. The active electrode assembly according to claim 1, further comprising:
   a counter electrode assembly, wherein the counter electrode assembly is configured for completing an electrical circuit between the active electrode assembly and an energy source; and an energy source for generating an electrical potential difference.

11. The active electrode assembly according to claim 1, wherein the active electrode includes an open-faced or high current density electrode.

12. An ocular iontophoretic device for delivering an interferon to an affected area of a living being's eye, comprising:

an active electrode assembly configured for placement proximate the affected area of the living being's eye, the active electrode assembly comprising:

an active electrode in electrical communication with a matrix, wherein the matrix is capable of temporarily retaining an interferon therein; and an interferon capable of treating viral, immunoregulatory, and/or neovascularization conditions retained within the matrix;

an energy source for generating an electrical potential difference in electrical communication with the active electrode assembly; and a counter electrode assembly in electrical communication with the energy source, and configured for placement on the living being, distal from the active electrode assembly;

such that, upon operative placement of the active electrode assembly and the counter electrode assembly, iontophoretic delivery of the interferon to the eye of the living being is enabled.

13. The ocular iontophoretic device according to claim 12, wherein the matrix includes an interferon selected from the group consisting of an alpha-interferon, a beta-interferon, a gamma-interferon, and mixtures thereof.

14. The ocular iontophoretic device according to claim 12, wherein the matrix includes a beta-interferon.

15. The ocular iontophoretic device according to claim 12, wherein the matrix includes a beta-1b interferon.

16. The ocular iontophoretic device according to claim 12, wherein the interferon comprises one or more natural or synthetic proteins having a molecular weight ranging from approximately 15,000 to approximately 25,000 daltons.

17. The ocular iontophoretic device according to claim 12, wherein the interferon is formulated in an approximately 20 mM sodium acetate and approximately 208 mM arginine hydrochloride buffer.

18. The ocular iontophoretic device according to claim 17, wherein the buffer ranges in pH from approximately 4.0 to approximately 6.0.

19. The ocular iontophoretic device according to claim 18, wherein the buffer ranges in pH from approximately 4.5 and approximately 5.0.

20. The ocular iontophoretic device according to claim 12, wherein the affected area of the eye is selected from at least one of the group consisting of the vitreous humor, retina, choroid, circulation of the retina, circulation of the choroid, and sclera.

21. The ocular iontophoretic device according to claim 12, wherein the active electrode assembly includes an open-faced or high current density electrode.

22. An ocular iontophoretic device for delivering an interferon to an affected area of a living being's eye, comprising:

a reservoir, wherein the reservoir includes an interferon capable of treating viral, immunoregulatory, and/or neovascularization conditions;

an active electrode assembly configured for placement proximate the affected area of the living being's eye, the active electrode assembly comprising:

an active electrode in electrical communication with a matrix, wherein the matrix is in fluidic communication with the reservoir, and is capable of temporarily retaining an interferon therein;

an energy source for generating an electrical potential difference in electrical communication with the active electrode assembly; and a counter electrode assembly in electrical communication with the energy source, and configured for placement on the living being, distal from the active electrode assembly;

such that, upon operative placement of the active electrode assembly and the counter electrode assembly, iontophoretic delivery of the interferon to the eye of the living being is enabled.

23. A method for treating an affected area of a living being's eye, comprising the steps of:

associating an interferon with an ocular iontophoretic device;

positioning at least a portion of the ocular iontophoretic device on the eye of a living being; and iontophoretically delivering the interferon to an affected area of the living being's eye.

24. The method according to claim 23, wherein the step of associating the interferon includes the step of associating an interferon capable of treating viral, immunoregulatory, and/or neovascularization conditions.

25. The method according to claim 23, wherein the step of iontophoretically delivering the interferon includes the step of iontophoretically delivering the interferon to at least one of the group consisting of the vitreous humor, retina, choroid, circulation of the retina, circulation of the choroid, and sclera.

26. The method according to claim 23, wherein the step of iontophoretically delivering the interferon includes the step of iontophoretically loading a sclera of the living being's eye with the interferon for prolonged delivery into back regions of the living being's eye.

27. The method according to claim 23, wherein the step of iontophoretically delivering the interferon includes the step of iontophoretically delivering the interferon at a current between approximately 0.5 mA and approximately 4 mA for a period of between approximately 5 and approximately 20 minutes.

28. The method according to claim 23, wherein the step of iontophoretically delivering the interferon includes the step of delivering the interferon using positive polarity electrical current.

29. The method according to claim 23, wherein the step of positioning at least a portion of the ocular iontophoretic device on the eye of a living being includes the step of applying at least a portion of the ocular iontophoretic device to a conjunctival surface in a region of a pars planum and/or insertions of an anterior cilliary artery.

30. A method for treating a viral, immunoregulatory, and/or neovascularization condition within an affected area of a living beings eye, comprising the steps of:

associating an interferon with a matrix of an ocular iontophoretic device;

associating the ocular iontophoretic device having an active electrode assembly with the eye of the living being;

iontophoretically delivering an effective amount of the interferon to an affected area of the living being's eye having a viral, immunoregulatory, and/or neovascularization condition; and treating the affected area of the living being's eye, and, in turn, reducing or eliminating effects of a viral, immunoregulatory, and/or condition.

31. The method according to claim 30, wherein the step of associating the interferon includes the step of associating an interferon capable of treating viral, immunoregulatory, and/or neovascularization conditions.

32. The method according to claim 30, wherein the step of iontophoretically delivering the interferon includes the step of iontophoretically delivering the interferon to at least one of the group consisting of the vitreous humor, retina, choroid, circulation of the retina, circulation of the choroid, and sclera.

33. The method according to claim 30, wherein the step of iontophoretically delivering the interferon includes the step of iontophoretically loading a sclera of the living being's eye with the interferon for prolonged delivery into back regions of the living being's eye.

34. The method according to claim 30, wherein the step of iontophoretically delivering the interferon includes the step of iontophoretically delivering the interferon at a current between approximately 0.5 mA and approximately 4 mA for a period of between approximately 5 and approximately 20 minutes.

35. The method according to claim 30, wherein the step of iontophoretically delivering the interferon includes the step of delivering the interferon using positive polarity electrical current.

36. The method according to claim 30, wherein the step of associating the ocular iontophoretic device having an active electrode assembly with the eye of the living being includes the step of applying at least a portion of the ocular iontophoretic device to a conjunctival surface in a region of a pars planum and/or insertions of an anterior cilliary artery.

* * * * *